United States Patent
Murakami et al.

(10) Patent No.: US 11,247,194 B2
(45) Date of Patent: Feb. 15, 2022

(54) METHOD FOR PRODUCING POROUS MOLDED BODY, METHOD FOR PRODUCING CATALYST FOR α-OLEFIN DIMERIZATION, METHOD FOR PRODUCING α-OLEFIN DIMER, POROUS MOLDED BODY, AND CATALYST FOR α-OLEFIN DIMERIZATION

(71) Applicant: MITSUI CHEMICALS, INC., Tokyo (JP)

(72) Inventors: Masami Murakami, Ichihara (JP); Naoya Takahashi, Nagareyama (JP); Ryo Niishiro, Funabashi (JP)

(73) Assignee: MITSUI CHEMICALS, INC., Tokyo (JP)

( * ) Notice: Subject to any disclaimer, the term of this patent is extended or adjusted under 35 U.S.C. 154(b) by 324 days.

(21) Appl. No.: 16/471,420

(22) PCT Filed: Dec. 21, 2017

(86) PCT No.: PCT/JP2017/046048
§ 371 (c)(1),
(2) Date: Jun. 19, 2019

(87) PCT Pub. No.: WO2018/117247
PCT Pub. Date: Jun. 28, 2018

(65) Prior Publication Data
US 2021/0113991 A1    Apr. 22, 2021

(30) Foreign Application Priority Data
Dec. 22, 2016 (JP) .............................. JP2016-249237

(51) Int. Cl.
*B01J 23/04* (2006.01)
*B01J 27/232* (2006.01)
(Continued)

(52) U.S. Cl.
CPC ............... *B01J 23/04* (2013.01); *B01J 21/18* (2013.01); *B01J 27/232* (2013.01); *B01J 35/002* (2013.01);
(Continued)

(58) Field of Classification Search
CPC . B01J 23/04; B01J 21/18; B01J 35/002; B01J 35/026; B01J 35/1038;
(Continued)

(56) References Cited

U.S. PATENT DOCUMENTS 5,081,094 A      1/1992  Drake
2010/0312035 A1* 12/2010 Ruettinger ............. B01J 23/002
                                                          585/852
(Continued)

FOREIGN PATENT DOCUMENTS

EP    3075448 A1    10/2016
JP    S58114737 A   7/1983
(Continued)

OTHER PUBLICATIONS

International Search Report dated Mar. 27, 2018 filed in PCT/JP2017/046048.
(Continued)

*Primary Examiner* — Ali Z Fadhel
(74) *Attorney, Agent, or Firm* — Rankin, Hill & Clark LLP (57) ABSTRACT

Provided is a method of producing a porous molded body, the method including: the step of obtaining a molded body by molding a raw material that contains from 1 part by mass to 100 parts by mass of a bicarbonate compound (A) represented by $AHCO_3$ (wherein, A represents Na or K) and from 0 parts by mass to 99 parts by mass of a compound (B) represented by $B_nX$ (wherein, B represents Na or K; X represents $CO_3$, $SO_4$, $SiO_3$, F, Cl, or Br; and n represents an
(Continued)

integer of 1 or 2 as determined by the valence of X) (provided that a total amount of (A) and (B) is 100 parts by mass); and the step of obtaining a porous molded body by performing a heat treatment of the molded body in a temperature range of from 100° C. to 500° C. and an atmosphere that contains water vapor in an amount of from 1.0 g/m$^3$ to 750,000 g/m$^3$ and thereby thermally decomposing not less than 90% by mass of the bicarbonate compound (A).

8 Claims, 2 Drawing Sheets

(51) Int. Cl.
  *B01J 35/10* (2006.01)
  *B01J 37/00* (2006.01)
  *B01J 37/10* (2006.01)
  *B01J 21/18* (2006.01)
  *B01J 35/00* (2006.01)
  *B01J 35/02* (2006.01)
  *B01J 37/08* (2006.01)
  *C07C 2/24* (2006.01)
(52) U.S. Cl.
  CPC ............ *B01J 35/026* (2013.01); *B01J 35/10* (2013.01); *B01J 35/1038* (2013.01); *B01J 37/00* (2013.01); *B01J 37/0018* (2013.01); *B01J 37/0063* (2013.01); *B01J 37/088* (2013.01); *B01J 37/10* (2013.01); *C07C 2/24* (2013.01); *C07C 2521/18* (2013.01); *C07C 2523/04* (2013.01)
(58) Field of Classification Search
  CPC .. B01J 37/0018; B01J 37/0063; B01J 37/088; B01J 27/232; B01J 35/10; B01J 37/00; B01J 37/10; B01J 37/082; B01J 37/0201; B01J 35/1019; C07C 2/24; C07C 2521/18; C07C 2523/04; C07C 2/08; C07C 11/113; C07B 61/00; C01D 7/12; C01D 7/38
  See application file for complete search history.

(56) References Cited

U.S. PATENT DOCUMENTS

2016/0296919 A1   10/2016   Ichikawa
2018/0133696 A1*  5/2018    Te ......................... B01J 35/002
2018/0161761 A1*  6/2018    Yeates ................. B01J 35/1038

FOREIGN PATENT DOCUMENTS

| | | |
|---|---|---|
| JP | S60042231 A | 3/1985 |
| JP | H03042043 A | 2/1991 |
| JP | H07222927 A | 8/1995 |
| JP | 2006326418 A | 12/2006 |
| JP | 2008149275 A | 7/2008 |
| KR | 10-2005-0001382 A | 1/2005 |
| KR | 10-2016-0086902 A | 7/2016 |
| WO | 2015093378 A1 | 6/2015 |

OTHER PUBLICATIONS

Extended European Search Report (EESR) dated Oct. 21, 2020 issued in the corresponding European Patent Application No. 17885428.7.

Korean Office Action (KROA) dated Oct. 12, 2020 issued in the corresponding Korean Patent Application No. 2019-7018261 and its partial English translation.

Fán, "Study of the Sintering-hydration and Crystallization to Heighten the Bulk Density of K2CO3", Data Base of Full Text of Excellent Thesis for Degree of Students in Graduate School of China, Process Techniques 1, Mar. 15, 2005, p39, total 4 pages; Cited in CNOA; Partial English translation in CNOA and discussed in CNOA.

Chinese Office Action (CNOA) dated Jul. 29, 2021 issued in corresponding Chinese Patent Application No. 201780079669.6 and its partial English translation.

* cited by examiner

FIG.1

US 11,247,194 B2

METHOD FOR PRODUCING POROUS MOLDED BODY, METHOD FOR PRODUCING CATALYST FOR α-OLEFIN DIMERIZATION, METHOD FOR PRODUCING α-OLEFIN DIMER, POROUS MOLDED BODY, AND CATALYST FOR α-OLEFIN DIMERIZATION

TECHNICAL FIELD

The present invention relates to: a method of producing a porous molded body; a method of producing an α-olefin dimerization catalyst; a method of producing an α-olefin dimer; a porous molded body; and an α-olefin dimerization catalyst.

BACKGROUND ART

As monomers for the production of polyolefins, α-olefin dimers typified by 4-methyl-1-pentene (including co-dimers; the same applies below) are utilized. Many basic catalysts have been conventionally proposed as catalysts for the production of corresponding dimers through α-olefin dimerization reactions (including co-dimerization reactions; the same applies below). Particularly, many catalysts obtained by supporting an alkali metal on a carrier containing an anhydrous potassium compound as a main component have been used.

With regard to these catalysts, it has been continuously studied to further enhance the activity and the selectivity to a target substance. In addition, since the catalyst life is not necessarily sufficient even when the initial activity is high, studies for extending the catalyst life have also been conducted continuously.

Moreover, the activity, the selectivity and the life of catalysts have been improved by adjusting the physical properties of anhydrous potassium compounds and carriers to be used. For example, Japanese Patent Application Laid-Open (JP-A) Nos. S58-114737, H3-42043, H7-222927, 2006-326418 and 2008-149275 as well as U.S. Pat. No. 5,081,094 disclose α-olefin dimerization catalysts.

Further, for example, WO 2015/093378 discloses a porous molded body used as a carrier of an α-olefin dimerization catalyst.

SUMMARY OF THE INVENTION

Technical Problem

The present inventors conducted various studies on catalysts typified by those disclosed in the above-described patent documents. As a result, it was revealed that, for example, the catalysts disclosed in JP-A Nos. S58-114737, H3-42043, H7-222927, 2006-326418 and 2008-149275 are observed with certain effects of improvement in terms of activity and selectivity; however, their carriers tend to collapse in long-term reactions, making continuous operation difficult.

In addition, for example, the catalyst using a potassium bicarbonate-containing carrier disclosed in U.S. Pat. No. 5,081,094 is in a powder form and thus not suitable for industrial production. Moreover, for example, U.S. Pat. No. 5,081,094 discloses that the carrier may be molded into the form of a pellet or the like; however, since the use of water in molding causes dissolution of potassium bicarbonate, it is inferred that the catalyst cannot be filled into a molding die smoothly and this makes the physical properties of the resulting molded body non-uniform.

Furthermore, for example, WO 2015/093378 discloses a method of producing a molded body that is porous and has a pore volume adjusted in a specific range (i.e., a porous molded body) as a molded body to be used as a carrier of an α-olefin dimerization catalyst. It is disclosed therein that the use of this molded body as a carrier of an α-olefin dimerization catalyst improves the reaction selectivity as compared to the use of a known catalyst.

For example, in the production of the porous molded body disclosed in WO 2015/093378, it is more desirable that the pore size is adjustable. More specifically, for example, there is a case where it is demanded to produce a porous molded body that has a pore size larger than that of a porous molded body obtained by the method disclosed in WO 2015/093378.

In view of the above, an object of the invention is to provide: a porous molded body that can be used as a carrier of an α-olefin dimerization catalyst, the porous molded body having excellent reaction selectivity in an α-olefin dimerization reaction and being adjusted to have a larger pore size; and a method of producing the same.

Another object of the invention is to provide: an α-olefin dimerization catalyst using the porous molded body; a method of producing the same; and a method of producing an α-olefin dimer using the catalyst.

Solution to Problem

The present disclosure encompasses the following embodiments.

<1> A method of producing a porous molded body, the method including:

the step of obtaining a molded body by molding a raw material that contains from 1 part by mass to 100 parts by mass of a bicarbonate compound (A) represented by $AHCO_3$ (wherein, A represents Na or K) and from 0 parts by mass to 99 parts by mass of a compound (B) represented by $B_nX$ (wherein, B represents Na or K; X represents $CO_3$, $SO_4$, $SiO_3$, F, Cl, or Br; and n represents an integer of 1 or 2 as determined by the valence of X) (provided that a total amount of (A) and (B) is 100 parts by mass); and the step of obtaining a porous molded body by performing a heat treatment of the molded body in a temperature range of from 100° C. to 500° C. and an atmosphere that contains water vapor in an amount of from 1.0 g/m³ to 750,000 g/m³ and thereby thermally decomposing not less than 90% by mass of the bicarbonate compound (A).

<2> The method of producing a porous molded body according to <1>, wherein the duration of the heat treatment is from 0.3 hours to 24 hours.

<3> The method of producing a porous molded body according to <1> or <2>, wherein the temperature of the heat treatment is in a range of from 100° C. to 300° C.

<4> The method of producing a porous molded body according to any one of <1> to <3>, wherein the heat treatment is performed in an atmosphere that contains water vapor in an amount of from 10.0 g/m³ to 750,000 g/m³.

<5> The method of producing a porous molded body according to any one of <1> to <4>, wherein not less than 97% by mass of the bicarbonate compound (A) is thermally decomposed by the heat treatment.

<6> The method of producing a porous molded body according to any one of <1> to <5>, wherein, when a total amount of the bicarbonate compound (A) and the compound (B) in the raw material is 100 parts by mass, the amount of the bicarbonate compound (A) is from 10 parts by mass to 100 parts by mass and that of the compound (B) is from 0 parts by mass to 90 parts by mass.

<7> The method of producing a porous molded body according to any one of <1> to <6>, wherein the raw material is molded by tableting.

<8> The method of producing a porous molded body according to any one of <1> to <7>, wherein when the raw material contains the compound (B), a mixture of the bicarbonate compound (A) and the compound (B) has a median diameter (d50) of from 5 μm to 600 in terms of volume statistical value, and when the raw material does not contain the compound (B), the bicarbonate compound (A) has a median diameter (d50) of from 5 μm to 600 μm in terms of volume statistical value.

<9> The method of producing a porous molded body according to any one of <1> to <8>, wherein a content ratio of particles having a particle size of 40 μm or smaller in the raw material is from 3% by mass to 30% by mass.

<10> The method of producing a porous molded body according to any one of <1> to <9>, wherein the bicarbonate compound (A) is potassium bicarbonate ($KHCO_3$).

<11> The method of producing a porous molded body according to any one of <1> to <10>, wherein the compound (B) is potassium carbonate ($K_2CO_3$).

<12> The method of producing a porous molded body according to any one of <1> to <11>, wherein the raw material further contains a graphite (C).

<13> A method of producing an α-olefin dimerization catalyst, the method including:

the step of producing a porous molded body by the method of producing a porous molded body according to any one of <1> to <12>; and the step of obtaining an α-olefin dimerization catalyst by supporting an alkali metal (D) on the porous molded body.

<14> A method of producing an α-olefin dimer, the method including:

the step of producing an α-olefin dimerization catalyst by the method of producing an α-olefin dimerization catalyst according to <13>; and the step of obtaining an α-olefin dimer by performing a dimerization reaction of an α-olefin in the presence of the α-olefin dimerization catalyst.

<15> A porous molded body including a carbonate compound (A1) that is at least either one of sodium carbonate ($Na_2CO_3$) and potassium carbonate ($K_2CO_3$), wherein pores having a pore diameter in a range of from 0.05 μm to 10 μm have a median pore size of larger than 0.36 μm but 0.90 μm or smaller, the pores having a pore diameter in a range of from 0.05 μm to 10 μm have a volume in a range of from 0.10 mL/g to 0.30 mL/g, and the porous molded body has a crushing strength of from 1.8 kgf to 8.5 kgf.

<16> The porous molded body according to <15>, wherein a content ratio of the carbonate compound (A1) is not less than 70% by mass with respect to a total amount of the porous molded body.

<17> The porous molded body according to <15> or <16>, further including at least one compound (B1) represented by $Na_nY$ or $K_nY$ (wherein, Y represents $SO_4$, $SiO_3$, F, Cl, or Br; and n represents an integer of 1 or 2 as determined by the valence of Y).

<18> The porous molded body according to any one of <15> to <17>, wherein the median pore size is in a range of from 0.40 μm to 0.90 μm.

<19> The porous molded body according to any one of <15> to <18>, wherein the volume of the pores is from 0.20 mL/g to 0.30 mL/g, and the crushing strength is from 2.2 kgf to 7.0 kgf.

<20> The porous molded body according to any one of <15> to <19>, wherein the carbonate compound (A1) is $K_2CO_3$.

<21> The porous molded body according to any one of <15> to <20>, further including a graphite (C).

<22> An α-olefin dimerization catalyst, in which an alkali metal (D) is supported on the porous molded body according to any one of <15> to <21>.

Effects of Invention

According to the disclosure, a method of producing a porous molded body that can be used as a carrier of an α-olefin dimerization catalyst, the porous molded body having excellent reaction selectivity in an α-olefin dimerization reaction and being adjusted to have a larger pore size, is provided.

Further, according to the disclosure, a method of producing an α-olefin dimerization catalyst using the porous molded body and a method of producing an α-olefin dimer using the catalyst are provided.

DETAILED DESCRIPTION OF THE INVENTION

Mode for Carrying Out the Invention

In the present specification, those numerical ranges that are expressed with "to" each denote a range that includes the numerical values stated before and after "to" as a lower limit value and an upper limit value, respectively.

In a set of numerical ranges that are stated in a stepwise manner in the present specification, the upper limit value or the lower limit value of a numerical range may be replaced with the upper limit value or the lower limit value of other numerical range. Further, in a numerical range stated in the present specification, the upper limit value or the lower limit value of the numerical range may be replaced with a value indicated in Examples.

In the present specification, the unit of crushing strength [kgf] can be converted into [N] based on a relational expression: 1 kgf=9.8 N.

In the present specification, the term "step" encompasses not only discrete steps but also steps that cannot be clearly distinguished from other steps, as long as the intended purpose of the step is achieved.

<Method of Producing Porous Molded Body>

The method of producing a porous molded body according to the disclosure (hereinafter, also referred to as "the production method of the disclosure") includes:

the step of obtaining a molded body by molding a raw material that contains from 1 part by mass to 100 parts by mass of a bicarbonate compound (A) represented by $AHCO_3$ (wherein, A represents Na or K) and from 0 parts by mass to 99 parts by mass of a compound (B) represented by $B_nX$ (wherein, B represents Na or K; X represents $CO_3$, $SO_4$, $SiO_3$, F, Cl, or Br; and n represents an integer of 1 or 2 as determined by the valence of X) (provided that a total amount of (A) and (B) is 100 parts by mass); and the step of obtaining a porous molded body by performing a heat treatment of the molded body in a temperature range of from 100° C. to 500° C. and an atmosphere that contains water vapor in an amount of from 1.0 g/m³ to 750,000 g/m³ and thereby thermally decomposing not less than 90% by mass of the bicarbonate compound (A).

By the studies conducted by the inventors, it was discovered that a porous molded body, which is obtained by molding a raw material containing the bicarbonate compound (A) and the compound (B) and subsequently thermally decomposing not less than 90% by mass of the bicarbonate compound (A) through a heat treatment of the thus obtained molded body in a specific temperature range and an atmosphere containing a specific amount of water vapor, not only simply has pores but also is adjusted to have a larger pore size. It was also discovered that the reaction selectivity of an α-olefin dimerization reaction is improved when this porous molded body is applied as a carrier of an α-olefin dimerization catalyst.

In other words, according to the production method of the disclosure, a porous molded body that has excellent reaction selectivity in an α-olefin dimerization reaction and can be used as a carrier of an α-olefin dimerization catalyst is obtained.

The reasons why the effects of the disclosure are obtained are speculated as follows; however, the production method of the disclosure should not be interpreted restrictively based on the below-described reasons.

In α-olefin dimerization reactions, there are cases where an α-olefin multimer is generated by a side reaction and pores of a catalyst are clogged by this multimer. Such clogging of pores is presumed to cause a reduction in the reaction selectivity of the α-olefin dimerization reactions.

According to the disclosure, it is believed that the structure of the porous molded body adjusted to have a larger pore size contributes to suppression of the generation of an α-olefin multimer in an α-olefin dimerization reaction. It is surmised that this inhibits clogging of pores of a catalyst caused by the multimer (i.e., by-product) and the reaction selectivity of the α-olefin dimerization reaction is consequently improved.

In the production method of the disclosure, the amount of water vapor in the water vapor-containing atmosphere during the heat treatment of the molded body is from 1.0 g/m³ to 750,000 g/m³, preferably from 10.0 g/m³ to 750,000 g/m³.

When the amount of water vapor is 1.0 g/m³ or greater, a porous molded body adjusted to have a larger pore size is more likely to be obtained. In addition, when the amount of water vapor is 1.0 g/m³ or greater, it is likely that the pore volume of the porous molded body is adjusted to be large as well.

When the amount of water vapor is 750,000 g/m³ or less, excellent production suitability is attained.

The lower limit value of the amount of water vapor is preferably 5.0 g/m³, more preferably 10.0 g/m³, still more preferably 12.0 g/m³.

The upper limit value of the amount of water vapor is preferably 100,000 g/m³, more preferably 10,000 g/m³, still more preferably 1,000 g/m³, particularly preferably 500 g/m³.

It is noted here that the term "bicarbonate compound (A)" used herein refers to a compound that is thermally decomposed during a heat treatment of a molded body to generate a gas such as water vapor.

In other words, in the production method of the disclosure, the phrase "an atmosphere that contains water vapor" refers to an atmosphere that contains a gas such as water vapor generated by thermal decomposition of the bicarbonate compound (A).

In the production method of the disclosure, the temperature at which the molded body is heat-treated (i.e., heat treatment temperature) is from 100° C. to 500° C.

When the heat treatment temperature is 100° C. or higher, the thermal decomposition of the bicarbonate compound (A) is facilitated, so that a porous molded body adjusted to have a larger pore size is more likely to be obtained. In addition, when the heat treatment temperature is 100° C. or higher, it is likely that the pore volume of the porous molded body is adjusted to be large as well.

Moreover, when the heat treatment temperature is 500° C. or lower, excellent production suitability is attained.

The heat treatment temperature is preferably from 100° C. to 400° C., more preferably from 100° C. to 300° C., still more preferably from 150° C. to 300° C., particularly preferably from 150° C. to 250° C.

In the production method of the disclosure, the duration of the heat treatment of the molded body (i.e., heat treatment time) is preferably 0.3 hours or longer.

The term "heat treatment time" used herein refers to a time required for the bicarbonate compound (A) to be thermally decomposed. The heat treatment may be continuously performed even after the completion of the thermal decomposition of the bicarbonate compound (A).

The heat treatment time is usually longer than the thermal decomposition time of the bicarbonate compound (A).

A method of determining the thermal decomposition time of the bicarbonate compound (A) will be described below in the section of Examples.

When the heat treatment time is 0.3 hours or longer, the thermal decomposition of the bicarbonate compound (A) is facilitated, so that a porous molded body adjusted to have a larger pore size is more likely to be obtained. In addition, it is likely that the pore volume of the porous molded body is adjusted to be large as well. The heat treatment time is more preferably 2 hours or longer from the standpoint of making it easier to control the heat treatment conditions.

The upper limit of the heat treatment time is not particularly restricted; however, it is preferably not longer than 24 hours from the standpoint of the heat treatment cost.

The heat treatment time is preferably from 0.3 hours to 24 hours, more preferably from 2 hours to 24 hours. A longer heat treatment time tends to result in a larger pore size. In other words, the pore size can be controlled by adjusting the heat treatment conditions.

The details of the heat treatment process will be described below.

The steps of the production method of the disclosure will now be described.

[Step of Obtaining Molded Body]

The step of obtaining a molded body is the step of obtaining a molded body by molding a raw material. The term "raw material" used herein refers to a raw material of a molded body.

(Raw Material)

The raw material contains from 1 part by mass to 100 parts by mass of a bicarbonate compound (A) represented by $AHCO_3$ (wherein, A represents Na or K), and from 0 parts by mass to 99 parts by mass of a compound (B) represented by $B_nX$ (wherein, B represents Na or K; X represents $CO_3$, $SO_4$, $SiO_3$, F, Cl, or Br; and n represents an integer of 1 or 2 as determined by the valence of X) (provided that a total amount of (A) and (B) is 100 parts by mass).

The constitution of the raw material encompasses a case where the amount of the compound (B) is 0 parts by mass, i.e., a case where the compound (B) is not contained in the raw material.

The reason for this is because, when the bicarbonate compound (A) is thermally decomposed during the heat treatment of the molded body and a gas such as water vapor is generated, pores are formed at those parts where the gas is generated, whereby a porous molded body adjusted to have a larger pore size can be obtained.

—Bicarbonate Compound (A)—

The bicarbonate compound (A) is represented by Formula $AHCO_3$.

In Formula $AHCO_3$, A represents Na or K. The bicarbonate compound (A) represented by Formula $AHCO_3$ is a compound that is at least either one of sodium bicarbonate ($NaHCO_3$) and potassium bicarbonate ($KHCO_3$). When the bicarbonate compound (A) contains both sodium bicarbonate ($NaHCO_3$) and potassium bicarbonate ($KHCO_3$), the mixing ratio thereof is not particularly restricted.

The amount of the bicarbonate compound (A) contained in the raw material is from 1 part by mass to 100 parts by mass, preferably from 10 parts by mass to 100 parts by mass, more preferably from 30 parts by mass to 100 parts by mass, still more preferably from 40 parts by mass to 100 parts by mass, particularly preferably from 40 parts by mass to 90 parts by mass, most preferably from 50 parts by mass to 90 parts by mass, with respect to a total of 100 parts by mass of the bicarbonate compound (A) and the compound (B).

From the standpoint of obtaining a porous molded body adjusted to have a larger pore size, the bicarbonate compound (A) is preferably potassium bicarbonate ($KHCO_3$) represented by the above-described Formula wherein A is K.

—Compound (B)—

The compound (B) is represented by Formula $B_nX$.

In Formula $B_nX$, B represents Na or K; X represents $CO_3$, $SO_4$, $SiO_3$, F, Cl, or Br; and n represents an integer of 1 or 2 as determined by the valence of X.

In other words, the compound (B) represented by Formula $B_nX$ is carbonate, sulfate, silicate, fluoride, chloride, or bromide of sodium or potassium. The compound (B) may be any one or more of compounds represented by $B_nX$. When the compound (B) is a mixture of two or more of such compounds, the mixing ratio thereof is not particularly restricted.

The amount of the compound (B) contained in the raw material is from 0 parts by mass to 99 parts by mass, preferably from 0 parts by mass to 90 parts by mass, more preferably from 0 parts by mass to 70 parts by mass, still more preferably from 0 parts by mass to 60 parts by mass, particularly preferably from 10 parts by mass to 60 parts by mass, most preferably from 10 parts by mass to 50 parts by mass, with respect to a total of 100 parts by mass of the bicarbonate compound (A) and the compound (B).

When X in Formula $B_nX$ is $SO_4$, $SiO_3$, F, Cl or Br, the amount of the compound (B) contained in the raw material is preferably 30 parts by mass or less, more preferably 20 parts by mass or less, still more preferably 10 parts by mass or less, with respect to a total of 100 parts by mass of the bicarbonate compound (A) and the compound (B).

Among the above-described compounds, the compound (B) is preferably potassium carbonate ($K_2CO_3$) represented by the above-described Formula wherein B is K, X is $CO_3$, and n is 2.

(Graphite (C))

The raw material may further contain a graphite (C).

When the raw material further contains the graphite (C) and the raw material containing the graphite (C) is molded by, for example, the below-described compression molding (e.g., tableting), the movement of a mortar and a pestle is likely to be smooth, so that the density of the resulting molded body is likely to be stable.

The characteristics of the graphite (C) are not particularly restricted, and any graphite may be used as long as it is generally used as a lubricant in molding.

Examples of such a graphite (C) that is generally used include graphites that have a median diameter (d50) in a range of from 5 μm to 500 μm in terms of volume statistical value and a specific surface area in a range of from 0.1 $m^2/g$ to 300 $m^2/g$ as measured by a BET method. The graphite (C) may be a natural graphite or an artificial graphite.

The amount of the graphite (C) to be added to the raw material can be set arbitrarily as long as the molding can be performed.

When the raw material contains the compound (B), the amount of the graphite (C) to be added to the raw material is preferably from 0.3 parts by mass to 10 parts by mass, more preferably from 0.5 parts by mass to 5 parts by mass, with respect to a total of 100 parts by mass of the bicarbonate compound (A) and the compound (B).

Meanwhile, when the raw material does not contain the compound (B), the amount of the graphite (C) to be added to the raw material is preferably from 0.3 parts by mass to 10 parts by mass, more preferably from 0.5 parts by mass to 5 parts by mass, with respect to 100 parts by mass of the bicarbonate compound (A).

When the added amount of the graphite (C) is 10 parts by mass or less, the strength of the resulting molded body is unlikely to be reduced. With the added amount of the graphite (C) being 0.3 parts by mass or greater, for example, an excessive increase in abrasion between a mortar and a pestle can be suppressed when the raw material is molded by tableting. This allows an apparatus to operate in a favorable manner, so that the density of the resulting molded body is likely to be stable.

Accordingly, when the added amount of the graphite (C) is in the above-described range, a molded body can be favorably molded. Consequently, the strength of a porous molded body obtained by heat-treating the molded body is likely to be ensured.

The raw material of the molded body may also contain, as required, a compound other than the above-described bicarbonate compound (A), compound (B) and graphite (C) within a range that does not impair the effects of the disclosure.

Examples of such other compound include ammonium bicarbonate. When the raw material contains ammonium bicarbonate, the pore volume of the resulting porous molded body can be further increased.

(Characteristics of Raw Material)

When the raw material contains the compound (B), the median diameter (d50) of a mixture of the bicarbonate compound (A) and the compound (B) is preferably from 5 μm to 600 μm, more preferably from 20 μm to 500 μm, still more preferably from 50 μm to 450 μm, particularly preferably from 50 μm to 300 μm, in terms of volume statistical value.

When the raw material does not contain the compound (B), the median diameter (d50) of the bicarbonate compound (A) is preferably from 5 μm to 600 μm, more preferably from 20 μm to 500 μm, still more preferably from 50 μm to 450 μm, particularly preferably from 50 μm to 300 μm, in terms of volume statistical value.

A powder having a median diameter in a range of from 5 μm to 600 μm has a favorable fluidity and is thus capable of yielding a molded body in a stable manner.

The content ratio of particles having a particle size of 40 μm or smaller in the raw material is preferably from 3% by mass to 30% by mass.

It is generally known that small-sized particles are desired to be removed because of their poor movement during tableting, and it is thus preferred to control the content ratio of particles having a particle size of 40 μm or smaller to be in the above-described range. When the content ratio of particles having a particle size of 40 μm or smaller is in the above-described range, the fluidity of the raw material is ensured, so that blocking is unlikely to occur and the raw material can be uniformly and easily loaded at the time of molding the raw material.

It is noted here that the particle size distribution of the bicarbonate compound (A) and that of the compound (B) may be different as long as the content ratio of particles having a particle size of 40 μm or smaller is in a range of from 3% by mass to 30% by mass in the mixture of the bicarbonate compound (A) and the compound (B).

(Molding of Raw Material)

In the disclosure, a method of molding the raw material is not particularly restricted and, for example, extrusion molding, compression molding, or granulation molding is employed. It is noted here that, since the bicarbonate compound (A) dissolves in water, it is preferred not to add water to the raw material (i.e., the raw material contains no water).

Among the above-described molding methods, from the standpoint of the characteristics of the raw material, the raw material is molded preferably by compression molding, particularly preferably by tableting.

When the raw material is molded by compression molding, the raw material is usually filled into a mortar serving as a die and compressed with a pestle to be molded.

Meanwhile, when the raw material is molded by tableting, since the raw material is uniformly filled into a mortar, a molded body with a small variation in density tends to be obtained.

When the raw material is molded by extrusion molding, a molding raw material which is imparted with enough viscosity to maintain its shape by an addition of a liquid to the raw material is molded through a die. In the case of molding the raw material by extrusion molding, since the bicarbonate compound (A) dissolves in water, it is preferred to use an organic solvent or the like in which the bicarbonate compound (A) does not dissolve.

When the raw material is molded by tableting, the density of the resulting tablet molded body is preferably from 1.6 g/mL to 2.3 g/mL, more preferably from 1.8 g/mL to 2.2 g/mL. The density of the tablet molded body can be adjusted by controlling the compression strength.

The size and the shape of the molded body are not particularly restricted. The shape of the molded body can be selected based on the conditions of a molding apparatus and the like, and the molded body may assume any of a noodle shape, a cylindrical shape, a convex shape, a ring shape, and a spherical shape.

When the raw material is molded by tableting, the shape of the resulting molded body is preferably a cylindrical shape, a convex shape or a ring shape, and it is more preferably a cylindrical shape from the standpoints of the ease of molding and the strength.

As a tableting apparatus, any commercially available tableting apparatus can be used. The tableting apparatus may be of a rotary type or a press type, and an apparatus of an optimum scale can be selected as appropriate in accordance with the production amount. When the raw material is molded into a cylindrical shape using a tableting apparatus, the resulting molded body usually has a size of from 2 mm to 5 mm in diameter and from 2 mm to 6 mm in height.

When the size of the molded body is in this range, an excessive reduction in the size of the molded body is inhibited, so that an increase in the number of tableting operations can be suppressed. Consequently, the productivity is improved and the cost can be reduced.

Moreover, with the size of the molded body being in the above-described range, when the molded body is heat-treated and subsequently applied as a carrier of an α-olefin dimerization catalyst or the like, the raw material and the product are likely to favorably diffuse in the reaction system, and the activity and the selectivity of α-olefin dimerization reaction are thus likely to be improved.

[Step of Obtaining Porous Molded Body]

The production method of the disclosure includes the step of obtaining a porous molded body by performing a heat treatment of the molded body in a temperature range of from 100° C. to 500° C. and an atmosphere that contains water vapor in an amount of from 1.0 $g/m^3$ to 750,000 $g/m^3$ (preferably from 10.0 $g/m^3$ to 750,000 $g/m^3$) and thereby thermally decomposing not less than 90% by mass of the bicarbonate compound (A).

The preferred range of the heat treatment temperature is as described above.

In the step of obtaining a porous molded body, the molded body is heat-treated in the above-described temperature range and an atmosphere that contains water vapor in the above-described range, whereby preferably not less than 97% by mass, more preferably not less than 98% by mass, still more preferably not less than 99% by mass of the bicarbonate compound (A) is thermally decomposed.

The thermal decomposition rate of the bicarbonate compound (A) in the heat treatment of the molded body is adjusted by the amount of water vapor in the water vapor-containing atmosphere, the heat treatment temperature, and the heat treatment time. When the heat treatment temperature is relatively low, the above-described thermal decomposition rate can be attained by extending the heat treatment time. By controlling the thermal decomposition rate of the bicarbonate compound (A) in the above-described range, a porous molded body adjusted to have a larger pore size is likely to be obtained. In addition, it is likely that the pore volume of the porous molded body is adjusted to be large as well. As a result, when the porous molded body is applied as a carrier of an α-olefin dimerization catalyst, the selectivity of α-olefin dimerization reaction is improved.

In the heat treatment of the molded body, examples of a method of heat-treating the molded body in an atmosphere that contains water vapor in an amount of from 1.0 $g/m^3$ to 750,000 $g/m^3$ (preferably from 10.0 $g/m^3$ to 750,000 $g/m^3$) include a method of performing the heat treatment while introducing water vapor to a heat treatment apparatus; a method of performing the heat treatment while introducing air (ambient air) to a heat treatment apparatus; a method of performing the heat treatment using a heat treatment apparatus having a hermetically closed structure; a method of performing the heat treatment by setting, for example, a crucible in which the molded body is placed and which is subsequently covered with a lid, in a heat treatment apparatus; and combinations of these methods.

In other words, it is preferred to perform the heat treatment of the molded body in an atmosphere that contains a gas such as water vapor generated by thermal decomposition of the bicarbonate compound (A) contained in the molded body, while allowing the generated gas such as water vapor to remain.

The specifications and the structure of the heat treatment apparatus are not particularly restricted, and any commonly-used heating furnace, electric furnace, belt furnace, hot-air circulating furnace or the like can be employed.

A method of determining the amount of water vapor during the heat treatment of the molded body (i.e., the amount of water vapor in the water vapor-containing atmosphere) will be described below in the section of Examples.

(Porous Molded Body)

In the production method of the disclosure, the porous molded body of the disclosure is obtained through the step of obtaining a molded body and the step of obtaining a porous molded body.

The porous molded body of the disclosure contains a carbonate compound (A1) that is at least either one of sodium carbonate ($Na_2CO_3$) and potassium carbonate ($K_2CO_3$).

In the porous molded body, pores having a pore diameter in a range of from 0.05 μm to 10 μm have a median pore size of larger than 0.36 μm but 0.90 μm or smaller and the pores having a pore diameter in a range of from 0.05 μm to 10 μm have a volume in a range of from 0.10 mL/g to 0.30 mL/g, and the porous molded body has a crushing strength of from 1.8 kgf to 8.5 kgf.

The porous molded body contains the carbonate compound (A1) that is at least either one of sodium carbonate ($Na_2CO_3$) and potassium carbonate ($K_2CO_3$).

The carbonate compound (A1) is produced in the porous molded body by the generation of a gas such as water vapor caused by thermal decomposition of the bicarbonate compound (A) during the heat treatment of the molded body.

When the carbonate compound (A1) is a mixture of sodium carbonate ($Na_2CO_3$) and potassium carbonate ($K_2CO_3$), the mixing ratio thereof is not particularly restricted.

The carbonate compound (A1) is preferably potassium carbonate ($K_2CO_3$).

The content ratio of the carbonate compound (A1) is preferably not less than 70% by mass, more preferably not less than 80% by mass, still more preferably not less than 90% by mass, with respect to a total amount of the porous molded body.

When the compound (B) is contained in the raw material yielding the molded body, the porous molded body may further contain at least one compound (B1) represented by Formula $Na_nY$ or $K_nY$ (wherein, Y represents $SO_4$, $SiO_3$, F, Cl, or Br; and n represents an integer of 1 or 2 as determined by the valence of Y). In other words, the compound (B1) is sulfide, silicate, fluoride or bromide of sodium or potassium.

The compound (B1) may be any one of compounds represented by Formula $Na_nY$ or $KEY$, or may be a mixture of two or more of such compounds. When the compound (B1) is a mixture of two or more of such compounds, the mixing ratio thereof is not particularly restricted.

When the compound (B1) is contained in the porous molded body, the content ratio of the compound (B1) is preferably higher than 0% by mass but 30% by mass or lower, more preferably higher than 0% by mass but 20% by mass or lower, still more preferably higher than 0% by mass but 10% by mass or lower.

When the raw material contains a graphite (C), the porous molded body may further contain the graphite (C). The graphite (C) added to the raw material may be oxidized depending on the temperature and the atmosphere in the heat treatment of the molded body; however, an arbitrary amount of the graphite (C) added to the raw material may remain in the porous molded body.

When the graphite (C) is contained in the porous molded body, the content ratio thereof is preferably higher than 0% by mass but 10% by mass or lower, more preferably higher than 0% by mass but 5% by mass or lower.

—Median Pore Size—

From the standpoint of improving the reaction selectivity when the porous molded body is applied as a carrier of an α-olefin dimerization catalyst, the median pore size of the porous molded body is preferably larger than 0.36 μm, more preferably 0.40 μm or larger. From the standpoint of the production suitability, the upper limit value of the median pore size is preferably 0.90 μm.

The median pore size is defined as a value that is calculated from measured sizes of pores having a pore diameter (i.e., pore size) in a range of from 0.05 μm to 10 μm. A method of determining the median pore size will be described below in the section of Examples.

—Pore Volume—

From the standpoint of improving the reaction selectivity when the porous molded body is applied as a carrier of an α-olefin dimerization catalyst, the pore volume of the porous molded body is preferably from 0.10 mL/g to 0.30 mL/g, more preferably from 0.25 mL/g to 0.30 mL/g, still more preferably from 0.20 mL/g to 0.30 mL/g.

The pore volume can be adjusted by, for example, adjusting the density of the tablet molded body.

The pore volume is defined as a volume of pores having a pore diameter (i.e., pore size) in a range of from 0.05 μm to 10 μm. A method of determining the pore volume will be described below in the section of Examples.

—Crushing Strength—

The crushing strength of the porous molded body is preferably not less than 1.8 kgf, more preferably not less than 2.2 kgf, still more preferably not less than 3.0 kgf. From the standpoint of the production suitability, the upper limit value of the crushing strength is 8.5 kgf or 7.0 kgf.

The term "crushing strength" used herein represents the strength of the porous molded body in the radial direction. The above-described noodle shape, cylindrical shape, convex shape, ring shape and spherical shape all have a direction corresponding to the radial direction. When the porous molded body has a shape without a direction corresponding to the radial direction, the strength in the direction having the lowest strength is defined as the crushing strength.

The crushing strength is generally known as a physical property that represents the compressive strength of a granule, and it is usually determined by pressing a single molded body of interest, such as a pellet or a tablet, in its barrel direction and measuring the force when the molded body is crushed. A test method thereof is prescribed in JIS Z8841 (1993) "Granules and Agglomerates—Test Methods for Strength".

In the production method of the disclosure, after molding the raw material containing the bicarbonate compound (A) and the compound (B), the thus obtained molded body is heat-treated in the above-described temperature range and an atmosphere that contains a specific amount of water vapor, whereby not less than 90% by mass of the bicarbonate compound (A) is thermally decomposed. As a result, a porous molded body adjusted to have a larger pore size is obtained.

In the prior art, the molded body is heat-treated while forcibly eliminating a gas such as water vapor generated by the thermal decomposition of the bicarbonate compound (A) so as to prevent retention of the generated gas. In contrast, in the production method of the disclosure, the molded body is heat-treated in an atmosphere that contains a specific amount of water vapor (i.e., while retaining the gas such as water vapor generated by the thermal decomposition of the bicarbonate compound (A)). Consequently, a porous molded body adjusted to have a larger pore size is obtained. In addition, it is likely that the pore volume of the porous molded body is adjusted to be large as well. Moreover, the strength of the porous molded body (e.g., crushing strength in the radial direction) is ensured.

When the porous molded body obtained in this manner is applied as a carrier of an α-olefin dimerization catalyst, the selectivity of α-olefin dimerization reaction is improved.

The porous molded body obtained by the production method of the disclosure can be preferably used as a carrier of an α-olefin dimerization catalyst, and it may also be used as a catalyst carrier other than a carrier of an α-olefin dimerization catalyst.

<Method of Producing α-Olefin Dimerization Catalyst>

The method of producing an α-olefin dimerization catalyst according to the disclosure includes: the step of producing a porous molded body by the above-described method of producing a porous molded body; and the step of obtaining an α-olefin dimerization catalyst by supporting an alkali metal (D) on the porous molded body.

In other words, according to this production method, an α-olefin dimerization catalyst having excellent selectivity in an α-olefin dimerization reaction can be obtained.

The alkali metal (D) is preferably sodium, potassium, or a mixture of sodium and potassium.

The term "alkali metal (D)" used herein refers to a non-ionized, zero-valent metal. The alkali metal (D) may contain a component other than an alkali metal when the purity of the alkali metal is 90% or higher. Examples of the component other than an alkali metal include the elements in Group I of the periodic table, such as lithium and potassium; various oxides and hydroxides; and metal elements other than the elements in Group I of the periodic table.

Various methods may be employed as a method of supporting the alkali metal (D) on a carrier composed of the porous molded body of the disclosure.

The temperature of a supporting treatment is usually in a range of from 150° C. to 400° C. From the standpoint of obtaining a catalyst that is excellent in catalytic activity, catalyst life and selectivity to α-olefin dimerization products, the temperature of the supporting treatment is preferably in a range of from 200° C. to 350° C., more preferably in a range of from 200° C. to 300° C. The atmosphere of the supporting treatment may be a reducing atmosphere or an inert atmosphere, as long as it is not a moist and oxidizing atmosphere. Taking into consideration the safety and the economic efficiency, the supporting treatment is preferably performed in a nitrogen atmosphere.

In the supporting treatment, the carrier composed of the porous molded body is preferably vibrated, rotated or stirred so as to allow the carrier to uniformly support the alkali metal (D). The supported alkali metal (D) is known to induce an exchange reaction with an alkali metal contained in the carrier when brought into contact with the carrier under heating.

The content ratio (support ratio) of the alkali metal (D) in the resulting α-olefin dimerization catalyst is usually in a range of from 0.5% by mass to 10% by mass, preferably in a range of from 1% by mass to 6% by mass, taking a total amount of the alkali metal (D) and the carrier as 100% by mass.

In this production method, a porous molded body adjusted to have a larger pore size is obtained by the step of producing a porous molded body. Since the support ratio of the alkali metal (D) and the catalytic activity correlate with each other, the porous molded body adjusted to have a larger pore size can support a greater amount of the alkali metal (D).

In other words, according to this production method, a highly active α-olefin dimerization catalyst can be obtained. In addition, when an α-olefin dimerization reaction is performed using this catalyst, the selectivity of the α-olefin dimerization reaction is improved. Generally, a higher activity tends to cause an increase in the load on the carrier and to thereby increase the possibility that collapse of the catalyst carrier (porous molded body) is facilitated; however, since strength (e.g., crushing strength in the radial direction) is ensured in the porous molded body, it is believed that the α-olefin dimerization catalyst is unlikely to collapse.

<Method of Producing α-Olefin Dimer>

The method of producing an α-olefin dimer according to the disclosure includes: the step of producing an α-olefin dimerization catalyst by the above-described method of producing an α-olefin dimerization catalyst; and the step of obtaining an α-olefin dimer by performing a dimerization reaction of an α-olefin in the presence of the α-olefin dimerization catalyst.

In other words, according to this production method, since a dimerization reaction of an α-olefin is performed in the presence of the α-olefin dimerization catalyst having excellent reaction selectivity, an α-olefin dimer can be obtained with a high yield.

Specific examples of the α-olefin include lower α-olefins, such as ethylene, propylene, 1-butene, isobutylene, and 1-pentene. Among dimerization reactions of these lower α-olefins, the α-olefin dimerization catalyst obtained by the production method of the disclosure is preferably used in the production of 4-methyl-1-pentene through dimerization of propylene and the production of 3-methyl-1-pentene through co-dimerization of 1-butene and ethylene.

The reaction temperature in the dimerization reaction of the α-olefin using the α-olefin dimerization catalyst obtained by the production method of the disclosure is usually from 0° C. to 300° C., preferably from 50° C. to 200° C.

Further, the reaction pressure is usually from normal pressure to 19.6 MPa (200 kg/cm$^2$-G), preferably in a range of from 1.96 MPa to 14.7 MPa (from 20 kg/cm$^2$-G to 150 kg/cm$^2$-G).

The state of the α-olefin in the dimerization reaction varies depending on the conditions of the dimerization reaction and the type of the α-olefin; however, the α-olefin may generally assume a liquid-phase state, a gas-phase state, or a supercritical state.

Among these states, the dimerization reaction is preferably performed with the α-olefin being in a gas-phase state or a supercritical state.

The dimerization reaction of the α-olefin can be performed in a fixed bed system or a fluidized bed system and, between these systems, the dimerization reaction is preferably performed in a fixed bed system. When the dimerization reaction is performed in a fixed bed system, the liquid hourly space velocity (LHSV) of the α-olefin is usually in a range of from 0.1 hr$^{-1}$ to 10 hr$^{-1}$, preferably in a range of from 0.5 hr$^{-1}$ to 5 hr$^{-1}$.

After the completion of the dimerization reaction, unreacted α-olefin and a product are separated from the resulting mixture in accordance with a conventional method, and the unreacted α-olefin is circulated and recycled for the reaction.

EXAMPLES

The invention will now be described concretely by way of Examples thereof; however, the present invention is not restricted thereto.

[Measurement of Median Diameter (d50)]

Mesh sieves having a mesh size of 850 μm, 500 μm, 300 μm, 212 μm, 100 μm, 53 μm or 20 μm were each prepared. Subsequently, in a glove box in which nitrogen was circulated, 30 g of a powder of interest was put on the upper part of each mesh sieve and manually sieved. Thereafter, the mass of the powder remaining on each mesh sieve was measured to determine the median diameter (d50).

[Measurement of Content Ratio of Particles Having Particle Size of 40 μm or Smaller]

In a glove box in which nitrogen was circulated, 30 g of a powder of interest was put on the upper part of a mesh sieve having a mesh size of 40 μm and manually sieved. The mass of the powder that passed through the sieve was measured, and the thus measured value was divided by the initial amount of 30 g to calculate the content ratio of particles having a particle size of 40 μm or smaller.

[Measurement of Thermal Decomposition Rate of Bicarbonate Compound (A)]

Using a differential thermo-gravimetric analyzer (manufactured by Rigaku Corporation, model: TG8120), a porous molded body obtained was heated to 400° C., and the amount of weight reduction was measured. From the relationship between the content of the bicarbonate compound (A) during molding and the thus measured amount of weight reduction, the thermal decomposition rate was calculated. Stoichiometrically, 1 mole of water and 1 mole of $CO_2$ are generated from 2 moles of the bicarbonate compound (A). When the thermal decomposition rate is 100% by mass, since no further thermal decomposition takes place, a reduction in weight is not observed on the differential thermo-gravimetric analyzer.

[Measurement of Pore Volume and Median Pore Size]

The volume of pores having a pore diameter (i.e., pore size) in a range of from 0.05 μm to 10 μm was measured by a mercury intrusion method using a mercury porosimeter (manufactured by MicroMetrics, Inc., model: AUTO PORE IV). Further, the sizes of pores in this range were measured, and the median pore size was determined from the thus measured values.

[Measurement of Crushing Strength of Porous Molded Body]

Using a digital hardness meter (manufactured by Fujiwara Scientific Company Co., Ltd., model: KHT-40N), the crushing strength of the porous molded body in the radial direction (i.e., in the barrel direction of the cylindrical molded body) was measured in accordance with the method prescribed in JIS Z8841 (1993) "Granules and Agglomerates—Test Methods for Strength".

In the principle of the measurement of the crushing strength, a cylindrical porous molded body to be measured is placed on a stationary sample table, and a movable pressing surface is lowered from above at a constant rate and pressed against the cylindrical porous molded body to measure the strength when the cylindrical porous molded body is broken.

Example 1

[Production of Porous Molded Body]

As a bicarbonate compound (A) and a compound (B), 60 parts by mass of potassium bicarbonate ($KHCO_3$) (manufactured by Junsei Chemical Co., Ltd., purity: 99%, catalog No.: 43300-1201) and 40 parts by mass of $K_2CO_3$ (purity: 99%, specific surface area measured by BET method: 1.3 m$^2$/g, bulk density: 0.46 g/mL), respectively, were mixed to obtain 100 parts by mass of a powder mixture. The median diameter (d50) of the thus obtained powder mixture and the content ratio of particles having a particle size of 40 μm or smaller are shown in Table 1.

It is noted here that the median diameter (d50) of the powder mixture and the content ratio of particles having a particle size of 40 μm or smaller are values determined by the above-described respective methods.

The powder mixture in an amount of 100 parts by mass was homogeneously mixed with 0.9 parts by mass of a graphite (purity: 98%, median diameter (d50): 0.6 μm, specific surface area measured by BET method: 150 m$^2$/g), and the resultant was used as a tableting raw material (i.e., a raw material of a molded body) which was subsequently tableted while controlling the compression strength such that the resulting tablet molded body had a density of 2.0 g/mL, whereby a tablet molded body having a cylindrical shape of 3 mm in diameter and 3 mm in height was obtained. Then, 116 kg of the thus obtained tablet molded body was placed in a tray, and the tray was put into a hot-air circulating furnace of 4 m$^3$ in capacity without covering the tray with a lid. The temperature of the furnace was raised from room temperature (e.g., 25° C.) to 155° C. at a rate of 65° C./h and then maintained for 12 hours, after which the temperature was further raised to 300° C. at a rate of 24° C./h and maintained at 300° C. for 1 hour, whereby a heat-treated molded body (i.e., porous molded body (1)) was obtained. The thermal decomposition rate of $KHCO_3$ was 100% by mass.

In the hot-air circulating furnace, the ambient air was introduced at a rate of 60 m$^3$/hr. Since the ambient air had a temperature of 25° C. and a relative humidity of 60%, the water vapor content (i.e., water vapor amount) of the ambient air is calculated to be about 13.9 g/m$^3$.

Since 116 kg of the tablet molded body contained about 69.0 kg of $KHCO_3$, the amount of water generated by thermal decomposition is calculated to be about 6.2 kg. Further, the total heating time was 21 hours; however, the heat treatment time (i.e., thermal decomposition time of $KHCO_3$) was estimated to be 15.5 hours from the temperature of the molded body.

Based on these values, the average water vapor content during the heat treatment is calculated as follows:

$$13.9 \text{ g/m}^3 + (6.2 \times 1{,}000 \text{ g}/(60 \text{ m}^3/\text{h} \times 15.5 \text{ hr}) \approx 20.6 \text{ g/m}^3.$$

The thermal decomposition time of $KHCO_3$ was specifically determined as follows.

The change in the molded body temperature was actually measured, and a point when the molded body temperature reached 100° C., which is the decomposition temperature of $KHCO_3$, was judged as the start of the thermal decomposition, while a point when the increase in the molded body temperature started to follow the increase in the temperature of the drying furnace was judged as the completion of the thermal decomposition of $KHCO_3$. Since the thermal decomposition of $KHCO_3$ is an endothermic reaction, the increase in the molded body temperature was slower than the increase in the atmospheric temperature during the continuation of the thermal decomposition reaction.

Table 1 shows the pore volume, the median pore size and the radial-direction crushing strength of the thus obtained porous molded body (1).

[Preparation of α-Olefin Dimerization Catalyst]

After drying 96.5 parts by mass of the porous molded body (1) in a nitrogen gas flow at 300° C. for 2 hours, 3.5 parts by mass of sodium was added thereto in a nitrogen gas flow, and the resultant was stirred at 280° C. for 3.5 hours to prepare an α-olefin dimerization catalyst (1).

Since no adhesion of the added sodium to its carrying container was observed, it was judged that the whole amount of sodium was supported on the porous molded body. The support ratio in this process was 3.5% by mass.

[Dimerization Reaction of Propylene]

The α-olefin dimerization catalyst (1) in an amount of 4 g, which was obtained by the above-described preparation method, was added to a single-tube reactor of 18 mm in diameter, and propylene was continuously fed to a catalyst layer at a reactor internal temperature of 140° C., a reaction pressure of 9.8 MPa and a propylene flow rate of 4 g/h to perform a synthesis reaction of 4-methyl-1-pentene (hereinafter, abbreviated as "4MP-1") through dimerization of propylene. The propylene conversion rate and the 4MP-1 selection rate in the execution of 180-hour flow reaction are shown in Table 1.

Example 2

A heat-treated molded body (i.e., porous molded body (2)) was obtained in the same manner as in Example 1, except that the mixing ratio of the bicarbonate compound (A) and the compound (B) was changed as shown in Table 1, that the amount of the tablet molded body placed in the tray was changed to 11 kg, and that the temperature of the furnace was raised from room temperature (e.g., 25° C.) to 100° C. at a rate of 75° C./h and subsequently further raised to 200° C. at a rate of 10° C./h and then to 300° C. at a rate of 16.6° C./h before being maintained at 300° C. for 1 hour, and the same operations as in Example 1 were performed thereafter. The results thereof are shown in Table 1.

Since 11 kg of the tablet molded body contained about 8.7 kg of $KHCO_3$, the amount of water generated by thermal decomposition is calculated to be about 0.78 kg.

Further, the $KHCO_3$ decomposition time, namely the heat treatment time, in a total heating time of 18 hours was estimated to be 10.0 hours. Based on these values, the average water vapor content during the heat treatment is calculated as follows:

$$13.9 \text{ g/m}^3 + (0.78 \times 1,000 \text{ g}/(60 \text{ m}^3/\text{h} \times 10.0 \text{ hr}) \approx 15.2 \text{ g/m}^3.$$

Example 3

A tablet molded body in an amount of 5 g, which was obtained in the same manner as in Example 2, was put into a crucible of 14 cm³ in capacity, and the crucible was covered with a lid and placed in an electric furnace. The temperature of the furnace was raised from room temperature (e.g., 25° C.) to 300° C. at a rate of 27° C./h and then maintained at 300° C. for 2 hours, whereby a heat-treated molded body (i.e., porous molded body (3)) was obtained. Table 1 shows the pore volume, the median pore size and the radial-direction crushing strength of the thus obtained porous molded body (3).

It is noted here that the pore volume, the median pore size and the radial-direction crushing strength of the porous molded body (3) are values determined by the above-described respective methods.

Water and carbon dioxide are generated by thermal decomposition of $KHCO_3$ during the heat treatment; however, since the crucible was not hermetically closed, the water vapor content in the crucible was determined as follows, assuming that the atmospheric pressure in the crucible was maintained at 1 atm.

First, the thermal decomposition time and the thermal decomposition temperature range of $KHCO_3$ were estimated in the same manner as in Example 1. The results thereof are shown in Table 1.

Next, assuming that water and carbon dioxide are generated at a volume ratio of 1:1 by thermal decomposition of $KHCO_3$ during the heat treatment (i.e., during the thermal decomposition), the amount of water "m" (unit: g) is calculated as follows, assuming that: with respect to a total pressure of 1 atm, water vapor partial pressure (P)=0.5 atm, volume (V)=1 m³=1,000 L, water molecular weight (M)=18 g/mol, ideal gas equation: PV=(m/M) RT (T: absolute temperature (unit: K)).

$$0.5 \text{ atm} \times 1,000 \text{ L} = m \text{ (g)}/18 \text{ (g/mol)} \times 0.0821 \text{ atm·L/(mol·K)} \times T$$

$$m \text{ (g)} = (0.5 \times 1,000 \times 18/0.0821)/T = 109622.4/T$$

By the above equations, the water vapor content is calculated to be about 294 g/m³ when T=373K (100° C.) and about 210 g/m³ when T=523K (i.e., 250° C.).

Example 4

A heat-treated molded body (i.e., porous molded body (4)) was obtained in the same manner as in Example 3, except that the heat treatment was performed by raising the temperature from room temperature (i.e., 25° C.) to 300° C. at a rate of 60° C./h and then maintaining the temperature at 300° C. for 2 hours, and the same operations as in Example 3 were performed thereafter. The results thereof are shown in Table 1.

Example 5

A heat-treated molded body (i.e., porous molded body (5)) was obtained in the same manner as in Example 3, except that the heat treatment was performed by raising the temperature from room temperature (i.e., 25° C.) to 300° C. at a rate of 550° C./h and then maintaining the temperature at 300° C. for 2 hours, and the same operations as in Example 3 were performed thereafter. The results thereof are shown in Table 1.

Example 6

A heat-treated molded body (i.e., porous molded body (6)) was obtained in the same manner as in Example 3, except that the heat treatment was performed by raising the temperature from room temperature (i.e., 25° C.) to 300° C. at a rate of 10° C./h and then maintaining the temperature at 300° C. for 2 hours, and the same operations as in Example 3 were performed thereafter. The results thereof are shown in Table 1.

Comparative Example 1

A heat-treated molded body (i.e., porous molded body (1C)) was obtained in the same manner as in Example 5, except that the crucible was not covered with a lid and a dry air having a water vapor content of 0.27 g/m³ was introduced, and the same operations as in Example 5 were performed thereafter. It is noted here that the average water vapor content during the heat treatment is estimated to be equivalent to the water vapor content in the dry air (i.e., 0.27 g/m³).

Further, in Comparative Example 1, an α-olefin dimerization catalyst was prepared in the same manner as in Example 1, and a dimerization reaction of propylene was performed using this α-olefin dimerization catalyst. The results thereof are shown in Table 1.

(i.e., 4MP-1) was improved as compared to the case where the catalyst produced from the porous molded body of Comparative Example 1 was used.

From these results, it is seen that the reaction selectivity in an α-olefin dimerization reaction is improved by using each of the porous molded bodies of Examples 1 to 2, which are adjusted to have a larger pore size, as a carrier of an α-olefin dimerization catalyst.

Figure 2:
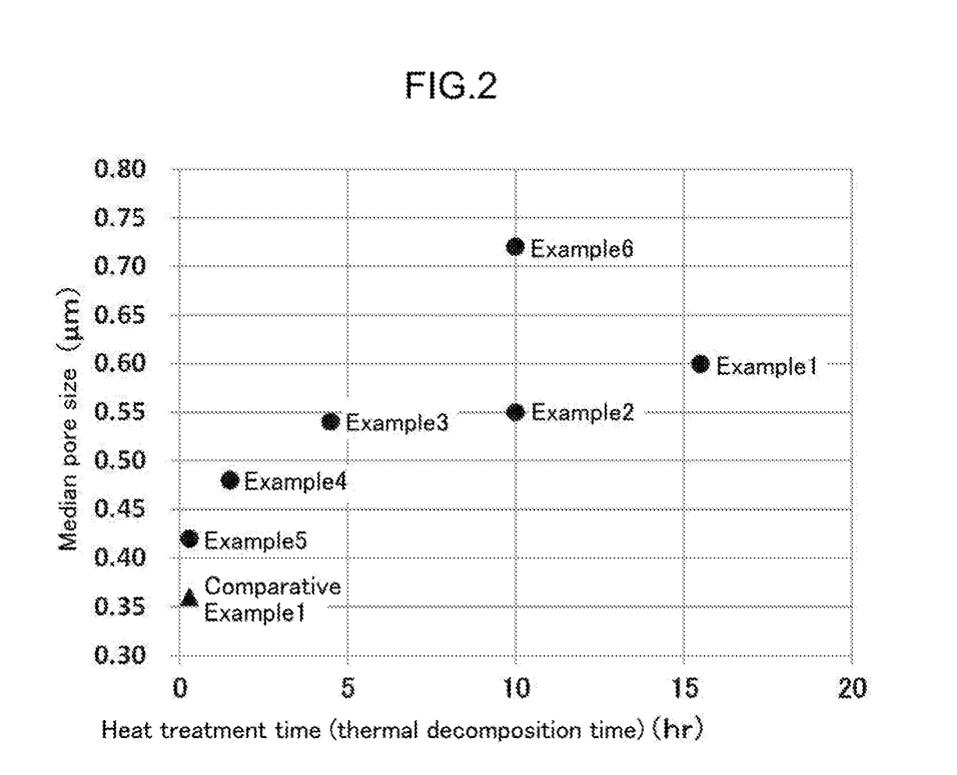
FIG. 2 is a graph showing the relationships between the heat treatment time (thermal decomposition time of $KHCO_3$) and the median pore size of the respective porous molded bodies in Examples and Comparative Example.

FIG. 2 shows the relationships between the heat treatment time (i.e., thermal decomposition time of $KHCO_3$) and the median pore size of the respective porous molded bodies in Examples and Comparative Example. As shown in FIG. 2, it is confirmed that the median pore size can be adjusted to be larger as the heat treatment time is extended. Moreover, it is confirmed that the median pore size tends to be larger as the water vapor content during the heat treatment is increased.

The disclosure of Japanese Patent Application No. 2016-249237 filed on Dec. 22, 2016, is hereby incorporated by reference in its entirety.

All the documents, patent applications and technical standards that are described in the present specification are hereby incorporated by reference to the same extent as if each individual document, patent application or technical standard is concretely and individually described to be incorporated by reference.

TABLE 1

| | | Example 1 | Example 2 | Example 3 | Example 4 | Example 5 | Example 6 | Comparative Example 1 |
|---|---|---|---|---|---|---|---|---|
| Raw material of molded body | Bicarbonate compound (A) $KHCO_3$ (parts by mass) | 60 | 80 | 80 | 80 | 80 | 80 | 70 |
| | Compound (B) $K_2CO_3$ (parts by mass) | 40 | 20 | 20 | 20 | 20 | 20 | 30 |
| | Median diameter d50 (μm) | 140 | 130 | 130 | 130 | 130 | 130 | 120 |
| | Content ratio of particles having a particle size of 40 μm or smaller (% by mass) | 3.0 | 6.0 | 6.0 | 6.0 | 6.0 | 6.0 | 7.5 |
| Heat treatment | Total heating time (hr) | 21 | 18 | 12 | 6.6 | 2.5 | 29.5 | 2.5 |
| | Heat treatment time (thermal decomposition time) (hr) | 15.5 | 10.0 | 4.5 | 1.5 | 0.3 | 10.0 | 0.3 |
| | Thermal decomposition rate of (A) (% by mass) | 100 | 100 | 100 | 100 | 100 | 100 | 100 |
| | Calculated value of water vapor content (g/m³) | 20.6 | 15.2 | 210 to 294 | 210 to 294 | 210 to 294 | 210 to 294 | 0.27 |
| Porous molded body | Pore volume (mL/g) | 0.21 | 0.25 | 0.26 | 0.25 | 0.24 | 0.25 | 0.21 |
| | Median pore size (μm) | 0.60 | 0.55 | 0.54 | 0.48 | 0.42 | 0.72 | 0.36 |
| | Crushing strength in radial direction (kgf) | 3.4 | 3.9 | 4.0 | 4.1 | 3.9 | 4.9 | 7.0 |
| Sodium support | Support ratio (% by mass) | 3.5 | 3.5 | — | — | — | — | 3.5 |
| Dimerization reaction | Propylene conversion rate (%) | 21.2 | 21.9 | — | — | — | — | 21.8 |
| | 4MP-1 selection rate (%) | 91.7 | 90.9 | — | — | — | — | 90.5 |

Figure 1:
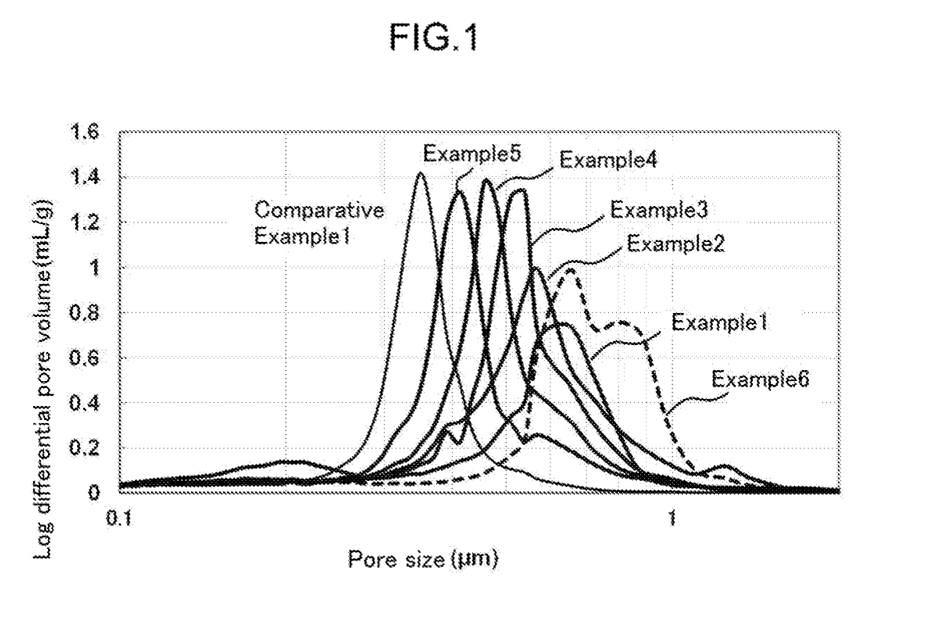
FIG. 1 is a graph showing the relationships between the pore size and the log differential pore volume in the porous molded bodies of Examples and Comparative Example.

FIG. 1 shows the relationships between the pore size and the log differential pore volume in the porous molded bodies of Examples and Comparative Example.

As shown in Table 1 and FIG. 1, in all of the porous molded bodies of Examples 1 to 6 that were each obtained by heat-treating a molded body containing the bicarbonate compound (A) and the compound (B) in an atmosphere containing from 1.0 g/m³ to 750,000 g/m³ of water vapor, the pore size (i.e., median pore size) was adjusted to be larger than that of the porous molded body of Comparative Example 1 that was obtained by heat-treating a molded body in a dry air (i.e., in an atmosphere containing 0.27 g/m³ of water vapor). Further, it is seen that the porous molded bodies of Examples 1 to 6 are observed with a tendency that not only the pore size but also the pore volume are adjusted to be large.

Moreover, in the α-olefin dimerization reactions using the catalysts produced from the porous molded bodies of Examples 1 and 2, the selectivity of 4-methyl-1-pentene

The invention claimed is:

1. A porous molded body comprising a carbonate compound (Al) that is at least either one of sodium carbonate ($Na_2CO_3$) and potassium carbonate ($K_2CO_3$), wherein
pores having a pore diameter in a range of from 0.05 μm to 10 μm have a median pore size of larger than 0.36 μm but 0.90 μm or smaller,
the pores having a pore diameter in a range of from 0.05 μm to 10 μm have a volume in a range of from 0.10 mL/g to 0.30 mL/g, and
the porous molded body has a crushing strength of from 1.8 kgf to 8.5 kgf.

2. The porous molded body according to claim 1, wherein a content ratio of the carbonate compound (Al) is not less than 70% by mass with respect to a total amount of the porous molded body.

3. The porous molded body according to claim 1, further comprising at least one compound (B1) represented by NanY or KnY (wherein, Y represents $SO_4$, $SiO_3$, F, Cl, or Br; and n represents an integer of 1 or 2 as determined by the valence of Y).

4. The porous molded body according to claim 1, wherein the median pore size is in a range of from 0.40 μm to 0.90 μm.

5. The porous molded body according to any claim 1, wherein
   the volume of the pores is from 0.20 mL/g to 0.30 mL/g, and
   the crushing strength is from 2.2 kgf to 7.0 kgf.

6. The porous molded body according to any claim 1, wherein the carbonate compound (Al) is $K_2CO_3$.

7. The porous molded body according to any claim 1, further comprising a graphite (C).

8. An a-olefin dimerization catalyst, in which an alkali metal (D) is supported on the porous molded body according to claim 1.

* * * * *

UNITED STATES PATENT AND TRADEMARK OFFICE
CERTIFICATE OF CORRECTION

PATENT NO. : 11,247,194 B2
APPLICATION NO. : 16/471420
DATED : February 15, 2022
INVENTOR(S) : Masami Murakami et al.

It is certified that error appears in the above-identified patent and that said Letters Patent is hereby corrected as shown below:

In the Claims

Column 21, Line 9 (Claim 5), delete "any" before claim 1.

Column 21, Line 14 (Claim 6), delete "any" before claim 1.

Column 21, Line 16 (Claim 7), delete "any claim" and insert --claim--.

Column 21, Line 20 (Claim 8), delete "claim" and insert --claim--.

Signed and Sealed this
Second Day of August, 2022

*Katherine Kelly Vidal*
Katherine Kelly Vidal
*Director of the United States Patent and Trademark Office*